United States Patent [19]
Stockhoff et al.

[11] Patent Number: 5,723,440
[45] Date of Patent: Mar. 3, 1998

[54] **CONTROLLING HEMIPTERAN INSECT PESTS WITH *BACILLUS THURINGIENSIS***

[75] Inventors: Brian Stockhoff; Christopher Conlan, both of San Diego, Calif.

[73] Assignee: Mycogen Corporation, San Diego, Calif.

[21] Appl. No.: 475,924

[22] Filed: Jun. 7, 1995

[51] Int. Cl.$^6$ .............. A01N 63/02; A61K 38/16; C12N 15/32; C12N 15/82
[52] U.S. Cl. .............. 514/12; 435/172.3; 435/252.5; 536/23.7; 800/205
[58] Field of Search ............ 424/93.461; 514/12; 435/172.3, 252.5, 252.41; 800/205

[56] References Cited

U.S. PATENT DOCUMENTS

| | | |
|---|---|---|
| 4,448,885 | 5/1984 | Schnepf et al. ............ 435/172.3 |
| 4,467,036 | 8/1984 | Schnepf et al. ............ 435/172.3 |
| 4,797,276 | 1/1989 | Hernstadt et al. ............ 435/69.1 |
| 4,849,217 | 7/1989 | Soares et al. ............ 424/93.461 |
| 4,853,331 | 8/1989 | Hernstadt et al. ............ 435/252.1 |
| 4,918,006 | 4/1990 | Ellar et al. ............ 435/69.1 |
| 4,948,734 | 8/1990 | Edwards et al. ............ 435/252.5 |
| 5,151,363 | 9/1992 | Payne ............ 435/252.5 |
| 5,262,159 | 11/1993 | Payne et al. ............ 424/93 |
| 5,273,746 | 12/1993 | Payne et al. ............ 435/252.5 |
| 5,298,245 | 3/1994 | Payne et al. ............ 435/252.1 |
| 5,302,387 | 4/1994 | Payne et al. ............ 435/252.5 |

FOREIGN PATENT DOCUMENTS

| | | |
|---|---|---|
| 0409438 | 1/1991 | European Pat. Off. |
| 931464 | 8/1993 | WIPO |

OTHER PUBLICATIONS

Beegle, C.C. (1978) "Use of Entomogenous Bacteria in Agroecosystems" Developments in Industrial Microbiologu 20:97–104.

Couch, T.L. (1980) "Mosquito Pathogenicity of Bacillus thuringiensis var. israelensis" Developments in Industrial Microbiology 22:61–76.

Feitelson, J.S. et al. (1992) "*Bacillus thuringiensis*: Insects and Beyond" Bio/Technology 10:271–275.

Gaertner, F.H. (1989) "Cellular Delivery Systems for Insecticidal Proteins: Living and Non–Living Microorganisms" Controlled Delivery of Crop–Protection Agents, pp. 245–257.

Gaertner, F., L. Kim (1988) "Current Applied Recombinant DNA Projects" TIBTECH 6(4):S4–S7.

Hofte, H., H.R. Whiteley (1989) "Insecticidal Crystal Proteins of *Bacillus thuringiensis*" Microbiological Reviews 53(2):242–255.

Krieg, V.A. et al. (1983) "*Bacillus thuringiensis* var. *tenebrionis*: A New Pathotype Effective Against Larvae of Coleoptera" Z. ang. Ent. 96:500–508.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

Jaquet, F. et al. (1987) "Specificity of *Bacillus thuringiensis* Delta–Endotoxin" Applied and Environmental Microbiology 53(3):500–504.

Prefontaine, G. et al. (1987) "Use of Oligonucleotide Probes to Study the Relatedness of Delta–Endotoxin Genes among *Bacillus thuringiensis* Subspecies and Strains" Applied and Environmental Microbiology 53(12):2808–2814.

Lambert, B. et al. (1992) "Novel *Bacillus thuringiensis* Insecticidal Crystal Protein with a Silent Activity against Coleopteran Larvae" Applied and Environmental Microbiology 58(8):2536–2542.

Cheung, P.Y.K. et al. (1985) "The Apparent in vivo Neuromuscular Effects of the ε–Endotoxin of *Bacillus thuringiensis* var. isrealensis in Mice and Insects of Four Orders" Pesticide Biochemistry and Physiology 23:85–94.

Tanigoshi, L.K. et al. (1990) "Efficacy of the β–Exotoxin of *Bacillus thuringiensis* to *Lygus hesperus* (Heteroptera: Miridae): Laboratory and Field Responses" Journal of Economic Entomology 83(6):2200–2206.

Farrag, R.M., F.N. Nasr (1992) "Efficacy of Chemical, Microbial Insecticides and Their Combinations Against the Cotton Seed Bug, *Oxycarenus hyalinipennis* Costs (Hemiptera:Lygaeidae)" Alex. Sci. Exch. 13(3):593–605.

Lima, M.M. et al. (1994) "Effects of the Spore–Endotoxin Complex of a Strain of *Bacillus thuringiensis* Serovar morrisoni upon *Triatoma vitticeps* (Hemiptera: Reduviidae) under Laboratory Conditions" Mem. Inst. Oswaldo Cruz 89(3):403–405.

Hofte, et al. (1989) Microbiological Reviews 53(2): 242–255.

*Primary Examiner*—Douglas W. Robinson
*Assistant Examiner*—Amy J. Nelson
*Attorney, Agent, or Firm*—Saliwanchik, Lloyd & Saliwanchik

[57] ABSTRACT

The subject invention concerns the use of *Bacillus thuringiensis* (B.t.) endotoxins to control hemipteran insect pests. Specifically exemplified is B.t. strain 201T6, B.t. var. israelensis, and δ-endotoxins therefrom. These isolates and toxins can be administered to said pests, or to the environment of said pests, e.g., plants, to achieve control of the pests. A preferred embodiment is the transformation of plants to express the B.t. toxins.

3 Claims, No Drawings

CONTROLLING HEMIPTERAN INSECT PESTS WITH *BACILLUS THURINGIENSIS*

DESCRIPTION

1. Field of the Invention

The present invention relates to methods for controlling insect pests of the order Hemiptera. In particular, δ-endotoxins of *Bacillus thuringiensis* (B.t.) have been discovered, unexpectedly, to control hemipteran insect pests, e.g., *Lygus hesperus*.

2. Background of the Invention

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner and Kim, 1988). Thus, isolated B.t. endotoxin genes are becoming commercially valuable.

Until the last fifteen years, commercial use of B.t. pesticides has been largely restricted to a narrow range of lepidopteran (caterpillar) pests. Preparations of the spores and crystals of *B. thuringiensis* var. kurstaki have been used for many years as commercial insecticides for lepidopteran pests. For example, *B. thuringiensis* var. kurstaki HD-1 produces δ-endotoxin crystals which are toxic to the larvae of a number of lepidopteran insects.

In recent years, however, investigators have discovered B.t. pesticides with specificities for a much broader range of pests. For example, other species of B.t., namely B.t. var. israelensis and B.t. var. tenebrionis (a.k.a. M-7, a.k.a. B.t. var. san diego), have been used commercially to control insects of the orders Diptera and Coleoptera, respectively (Gaertner, 1989). See also Couch, 1980 and Beegle, 1978. Krieg et al., 1983, describe *Bacillus thuringiensis* var. tenebrionis, which is reportedly active against two beetles in the order Coleoptera. These are the Colorado potato beetle, *Leptinotarsa decemlineata*, and the beetle *Agelastica alni*.

Recently, new subspecies of B.t. have been identified, and genes responsible for active δ-endotoxin proteins have been isolated (Höfte and Whiteley, 1989). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al., 1987, describe probes useful in classifying lepidopteran-active genes. The discovery of strains specifically toxic to other pests has been reported (Feitelson et al., 1992).

B.t. crystalline toxins are generally recognized as being protoxins, requiring either particular physicochemical conditions (i.e., pH, redox, ionic strength), or the action of certain proteases, or both, to generate an active toxin (Höfte and Whiteley, 1989). In most cases, the insect supplies conditions for activation of the toxin; however, cases have been documented where pre-solubilization or pre-proteolysis have been necessary for optimum activity (Jacquet et al., 1987) or detection of activity (Lambert et al., 1992).

The cloning and expression of a B.t. crystal protein gene in *Escherichia coil* has been described in the published literature (Schnepf and Whiteley, 1981). U.S. Pat. No. 4,448,885 and U.S. Pat. No. 4,467,036 both disclose the expression of B.t. crystal proteins in *E. coli*. U.S. Pat. Nos. 4,797,276 and 4,853,331 disclose *B. thuringiensis* var. tenebrionis (a.k.a. B.t. san diego, a.k.a. M-7) which can be used to control coleopteran pests in various environments. U.S. Pat. No. 4,918,006 discloses *Bacillus thuringiensis* var. israelensis toxins which are active against dipteran pests and reports that a protein of about 27 kD, and fragments thereof, are responsible for the dipteran activity. U.S. Pat. No. 4,849,217 discloses B.t. isolates which have activity against the alfalfa weevil. U.S. Pat. No. 5,151,363 and U.S. Pat. No. 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

Hemiptera represent a major group of insects that have not, to date, been effectively controlled by B.t. δ-endotoxins. Numerous hemipteran pest species, most notably Lygus species, cause considerable plant damage and economic loss each year.

Hemiptera ranks among the most economically destructive orders. See Arnett, R. H. Jr., 1985. Of all Hemiptera, the mirids (Hemiptera: Miridae; includes Lygus) are the most notorious crop pests. Feeding causes injury that weakens plants and is a mode of plant disease transmission. In addition to *L. hesperus*, other pest Lygus include: *L. lineolaris* (Beauv.) (=*L. oblineatus* (Say)), *L. pratensis* (L.), *L. rugulipennis* Popp., and the common green capsid (*Lygus pabulinus* (L)). Members of this genus are found variously on cotton, potato, sugar beet, celery, beans, peach, apple, alfalfa, pear, plum, quince and a variety of nursery stock, ornamental plants and vegetable crops. Specific Mirid pests include: the potato capsid *Calocoris norvegicus* (Gmel.), a pest of potato and brassicas (e.g., cabbage, cauliflower, broccoli, kale, Brussels sprout, turnip); the stack bug (also carrot plant bug) *Orthops campestris* (L.), a pest of carrot, celery, parsnip, parsley and dill; the apple capsid *Plesiocoris rugicollis* (Fall.), a pest of apple, currants and gooseberry; the tomato bug *Cyrtopeltis modestus* (Distant), a pest of tomatoes; the suckfly *Cyrtopeltis notatus* (Distant), a pest of tobacco; the white marked fleahopper *Spanagonicus albofasciatus* (Reuter), injurious to grass, with damage particularly noticeable on golf greens; the honeylocust plant bug *Diaphnocoris chlorionis* (Say), a pest of beets; the onion plant bug *Labopidicola allii* Knight, a pest of cultivated and wild onions; the cotton fleahopper *Pseudatomoscelis seriatus* (Reuter), found on cotton; the rapid plant bug *Adelphocoris rapidus* (Say), an occasional pest of cotton and legumes; the four-lined plant bug *Poecilocapsus lineatus* (Fabricius), often a pest of garden crops.

Other Hemipteran pests include:

Lygaeidae (seed bug family): chinch bug (*Blissus leucopterus* (Say)) is a pest of maize, sorghums, wheat, millets, rice, barley, rye and oats; false chinch bugs (Nysius spp., e.g., *N. ericae, N. raphanus* Howard) are pests of brassicas, beets and potato.

Pentatomidae (stink bug family): the brown stink bug, *Euschistus servus* (Say) is a pest of cotton. The green stink bug, *Nezara viridula* (L.) is a generalist pest of seedlings, especially vegetables and legumes; Eurygaster species, e.g., *E. austriaca* (Schr.) and *E. integriceps* (Put.) (wheat shield bug, Sunn pest, Senn bug) attack wheat and barley.

Coreidae (squash bug family): *Anasa tristis* (DeGreer) (squash bug) is a local pest of squash; *A. armigera* (Say) (horned squash bug) is an occasional pest of cultivated cucumber.

Pyrrhocoridae (red bug and cotton stainer family): the cotton stainer *Dysdercus suturellus* (Herrich-Schaeffer) is a pest of cotton.

Tingidae (lace bug family): *Corythucha arcuata* (Say) often is a pest of roses, maple, apple and chestnut. Other Corythucha species include the cotton lace bug, chrysanthemum lace bug, elm lace bug and hawthorn lace bug.

Belostomatidae (giant water bug family): members of this family are known to attack and suck the blood of fishes and therefore can be a pest in fish hatcheries.

Members of the Reduviidae and Cimicidae (including kissing bug and bed bugs, respectively) bite mammals and transmit diseases contractile by humans.

The digestive system of hemipterans is unusual among the insects in several ways: certain hydrolyric digestive enzymes are absent such as trypsin; the midgut lacks a peritrophic membrane, and there is no crop. These features reflect the liquid diet and sucking mode of feeding, subject to evolutionary constraints. Because of the differences in diet, feeding mode, and digestive physiology and biochemistry, one would not necessarily expect that proteins having insecticidal activity against leaf-chewing insects would also have activity against fluid-feeding Hemiptera.

*Bacillus thuringiensis* PS201T6, NRRL B-18750, deposited on Jan. 9, 1991, or a δ-endotoxin therefrom, was previously found to have activity against certain pests. For example, see U.S. Patent Nos. 5,273,746; 5,298,245; and 5,302,387, which disclose the use of B.t. PS201T6. B.t. isolates PS123D1 has been disclosed in EP 0 409 438. B.t. isolate PS71M3 has been disclosed in EP 0 626 809. The above patents do not disclose or suggest the use of any B.t. isolate to control hemipteran insect pests.

Practice of the present invention provides an alternative to control of hemipteran pests with chemical pesticides, thereby allowing more environmentally friendly insect management and providing a tool for management of insecticide resistance.

BRIEF SUMMARY OF THE INVENTION

The subject invention concerns the use of *Bacillus thuringiensis* (B.t.) δ-endotoxins to control hemipteran insect pests. Specifically exemplified herein is the use of the B.t. isolate PS201T6 and toxins therefrom to control the hemipteran insect pest *Lygus hesperus*. The use of B.t. var. israelensis isolates and toxins is also described.

The subject invention also includes the use of variants of the exemplified B.t. isolates and toxins which have substantially the same pesticidal properties as the exemplified isolates and toxins. These variants include mutant microbes. Procedures for making mutants are well known in the microbiological art. Ultraviolet light and chemical mutagens such as nitrosoguanidine are used extensively toward this end.

Recombinant hosts which have been transformed to express B.t. toxins can also be used according to the subject invention. These recombinant hosts may be, for example, microorganisms or plants.

According to the subject invention, hemipteran insect pests can be controlled using the B.t. isolate itself, variants of the B.t. isolates, δ-endotoxins obtained from said isolates, commercial preparations made from cultures of the isolates, or toxins produced by DNA of this isolate. In one embodiment, the toxins may be produced by DNA which has been transformed into another host. In a preferred embodiment, the transformed host is a plant.

BRIEF DESCRIPTION OF THE SEQUENCES

SEQ ID NO. 1 is the nucleotide sequence encoding an approximately 30 kDa toxin of PS201T6.

SEQ ID NO. 2 is the deduced amino acid sequence of an approximately 30 kDa toxin of PS201T6.

SEQ ID NO. 3 is the amino acid sequence of a truncated 201T6 toxin of about 25 kDa.

DETAILED DISCLOSURE OF THE INVENTION

The subject invention concerns the discovery of a new method for controlling hemipteran insect pests which involves contacting said pests with a *Bacillus thuringiensis* (B.t.) δ-endotoxin in a manner wherein the hemipteran insect ingests the δ-endotoxin. Specifically exemplified is the use of toxins from the B.t. isolate known as PS201T6. Also exemplified is the use of toxins from *Bacillus thuringiensis* var. israelensis (B.t.i.) isolates to control hemipteran pests.

The *Bacillus thuringiensis* isolate PS201T6 has the following characteristics in its biologically pure form and as compared to B.t. HD-1:

TABLE 1

Comparison of *B.t.* PS201T6 and *B.t.* HD-1

|  | *B.t.* PS201T6 | *B.t.* HD-1 |
| --- | --- | --- |
| Inclusions: | elliptical & bipyramid | bipyramid |
| Approximate molecular wt. of proteins by SDS-PAGE | 133,000 31,000 | 130,000 68,000 |
| Host range | Cockroaches Diptera Corn Rootworm | Lepidoptera |

The israelensis variety of B.t. is well known and readily recognized by those skilled in this art. Characteristics generally associated with the israelensis category of B.t. include dipteran activity, H14 serotype, and a protein pattern which includes an approximately 28 to 33 kD protein and, generally, additional proteins of about 70 kD and 130 kD. Other B.t. varieties which express israelensis-type toxins can also be used according to the subject invention. Such toxins would have a size similar to the toxins produced by B.t.i. and a similar activity profile, including dipteran activity. B.t. var. morrisoni serotype 8a, 8b have, for example, been reported to express B.t.i.-type toxins. An example of such an isolate is PS71M3. As used herein, the term "*Bacillus thuringiensis* var. israelensis toxin" includes toxins which are similar or related to toxins expressed by B.t.i. but which happen to be expressed by a different variety of B.t.

The isolate designated PS123D1 is specifically exemplified as a B.t.i. isolate useful according to the subject invention. Of particular interest in controlling hemipteran pests are toxins of approximately 28 to 33 kD of a B.t.i. isolate or, preferably, modified forms of this toxin. One embodiment of the subject invention involves the use of truncated forms of the 28 kDa PS123D1 toxin to control hemipterans. A specific example is the truncated toxin which has amino acids removed from the N-terminus and is about 25 kDa. As described herein, the truncated forms of the toxins can be obtained through treatment of B.t. culture supernatants and/ or by growing B.t. cultures under appropriate conditions to result in the production of activated toxins as a result of the advantageous effects of endogenous proteases. Other modifications which cause, for example, solubilization of the B.t. toxin can also be utilized to obtain highly active toxins.

The *Bacillus thuringiensis* isolate PS123D1 has the following characteristics in its biologically pure form:

TABLE 2

Characteristics of *B.t.* PS123D1

|  | B.t. PS123D1 |
| --- | --- |
| Inclusions: | amorphic |
| Approximate molecular wt. of proteins by SDS-PAGE | 133,000 |
|  | 127,000 |
|  | 72,000 |
|  | 28,000 |

The cultures disclosed in this application have been deposited in the Agricultural Research Service Patent Culture Collection (NRRL), Northern Regional Research Center, 1815 North University Street, Peoria, Ill. 61604, USA.

| Culture | Repository No. | Deposit date |
| --- | --- | --- |
| *Bacillus thuringiensis* PS201T6 | NRRL B-18750 | January 9, 1991 |
| *E. coli* NM522 (pMYC2362) | NRRL B-21018 | December 2, 1992 |
| *E. coli* NM522 (pMYC2357) | NRRL B-21017 | December 2, 1992 |
| *Bacillus thuringiensis* PS123D1 | NRRL B-21011 | October 13, 1992 |
| *Bacillus thuringiensis* PS71M3 | NRRL B-18930 | December 27, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are fled. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

In one preferred embodiment of the subject invention, a toxin from B.t. isolate PS201T6 is used to achieve control of hemipteran insect pests. In another preferred embodiment, the PS201T6 toxin is activated. Toxins can be activated by, for example, culturing the microbe, under conditions which facilitate the activation of said toxin by the action of compounds which exist naturally or are produced in said culture. Activation may also be achieved by adding a compound to a *Bacillus thuringiensis* strain PS201T6 culture, or a supernatant thereof, wherein said compound participates in the activation of said toxin either through direct action on said toxin or by facilitating the action of a second compound. The additional compound may be, for example, a protease, or a compound which raises the pH of the culture or supernatant.

*Bacillus thuringiensis* PS201T6 is now available to the public, without restriction, by virtue of the issuance of U.S. Pat. No. 5,273,746.

Genes and toxins. In one embodiment of the subject invention, genes which encode B.t. toxins active against hemipteran insect pests are used to transform a suitable host. The genes and toxins useful according to the subject invention include not only the full length sequences but also fragments of these sequences, variants, mutants, and fusion proteins which retain the characteristic pesticidal activity of the toxins specifically exemplified. As used herein, the terms "variants" or "variations" of genes refer to nucleotide sequences which encode the same toxins or which encode equivalent toxins having similar pesticidal activity. As used herein, the term "equivalent toxins" refers to toxins having the same or essentially the same biological activity against the target pests as the claimed toxins.

It would be apparent to a person skilled in this art, having the benefit of this disclosure, that genes encoding hemipteran-active toxins can be identified and obtained through several means. The genes can be obtained from the isolate deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect the pesticidal activity of the protein.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Recombinant hosts. The toxin-encoding genes harbored by the isolates disclosed herein can be introduced into a wide variety of microbial or plant hosts. Expression of the toxin gene results, directly or indirectly, in the production of the toxin. With suitable microbial hosts, e.g., Pseudomonas, the microbes can be applied to the situs of the pest, where they will proliferate and be ingested by the pest, resulting in control of the pest. Alternatively, the microbe hosting the toxin gene can be treated under conditions that prolong the activity of the toxin and stabilize the cell. The treated cell, which retains the toxic activity, then can be applied to the environment of the target pest. Methods for treatment of microbial cells are disclosed in U.S. Pat. Nos. 4,695,455 and 4,695,462, which are incorporated herein by reference.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Furthermore, materials and methods for introducing B.t. genes into plants in order to confer upon such plants the ability to produce insecticidal toxins are well known in the art. In a preferred embodiment, the B.t. genes are modified to facilitate optimal stability and expression in the selected plant host. In this regard, U.S. Pat. No. 5,380,831 is incorporated herein by reference.

Mutants. Mutants of the isolate described herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

Following are examples which illustrate procedures for practicing the present invention. These examples should not be construed as limiting. All percentages are by weight and all solvent mixture proportions are by volume unless otherwise noted.

Example 1—Culturing B.t. Strain PS201T6

A subculture of B.t. isolate strain PS201T6 can be used to inoculate the following peptone, glucose, and salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm. for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

Example 2—Production of Activated 201T6 Toxin (201T6-D)

Activated 201T6 toxin can be produced by a variety of methods which result in truncation of the 201T6 toxin. In this regard, reference can be made to WO95/02693. In one such method, cultures of PS201T6 were harvested by centrifugation and resuspended to ⅕th to ¹/₂₅th of their original culture volume in 0.1 $Na_2CO_3/NaHCO_3$ pH 11.0 containing 0.5 mg/ml pronase E (Sigma Chemical Company, P-5147 Type XIV bacterial protease from *Streptomyces griseus*). The suspension was incubated at 37° C. overnight with mixing. The suspensions were dialyzed against 2 changes of 50 to 100 volumes each of either distilled water or 0.1 M $Na_2CO_3/NaHCO_3$ pH 9.5 to yield "dialyzed suspensions."

The suspension resulting from 0.1 M $Na_2CO_3/NaHCO_3$ pH 9.5 dialysis was centrifuged to remove cells, spores, and debris. Additional purification from spores and debris can be accomplished by filtration through a Whatman glass microfibre filter, a 0.8 micron cellulose acetate filter, and a 0.2 micron cellulose acetate filter to yield a "filtered supernatant."

Dried preparations of the processed toxin were prepared either before or after filtration by dialyzing against 2 changes of 50 to 100 volumes distilled water, followed by lyophilization (lyophilized, pronase-treated toxin).

Example 3—Alternative Method for Production of Activated 201T6 Toxin

Cultures of PS201T6 were harvested by centrifugation and resuspended to ⅕th to ¹/₂₅th of their original culture volume in 0.1M $Na_2CO_3/NaHCO_3$, 0.5% 2-mercaptoethanol, pH 11.0. The suspension was incubated for about 2 hours at room temperature. The suspension was centrifuged to remove cells, spores, and debris. Additional purification from spores and debris can be accomplished by filtration through a Whatman glass microfibre filter, a 0.8 micron cellulose acetate filter, and a 0.2 micron cellulose acetate filter to yield a "filtered supernatant." The suspensions were dialyzed against 2 changes of 50 to 100 volumes each of either distilled water or 0.1M $Na_2CO_3/NaHCO_3$ pH 9.5 to yield "dialyzed suspensions."

Dried preparations of the processed toxin were prepared either before or after filtration by dialyzing against two changes of 50 to 100 volumes distilled water, followed by lyophilization. Material prepared according to this procedure is referred to herein as 201T6-D.

Example 4—Activity of B.t. Isolates Against the Hemipteran Insect *Lygus hesperus*

Five newly-emerged (≦ one week old) *L. hesperus* adults were placed in a 1.0 oz. plastic portion cup (Fabrikal Corp.) with two pinholes in the side to allow gas exchange. A small piece of Scott MICROWIPES tissue was placed in the bottom of the cup to absorb liquid excreta. In place of a lid, two pieces of PARAFILM were stretched across the top, sandwiching in between them 200 μL of test solution. "Autoprocessed" B.t. PS201T6 cell culture broth (activated by resident proteases as described in Example 3) was presented to *L. hesperus* adults. The autoprocessed broth was estimated to contain approximately 4.5 mg/ml of toxin. 1 ml of the broth was diluted to 100 ml with a 15% sucrose solution. 200 μl of the resulting 45 μg/ml solution was used as the test solution. Insects were allowed to feed for three days. Mortality after three days was compared with that of starved insects and control insects provided a "blank" of 15% sucrose solution that contained no toxin. After establishing activity of 45 μg/ml. B.t. PS201T6 after three days, a subsequent experiment was conducted to establish activity of 10 μg/mL, after two days. Representative results are shown in Tables 3 and 4.

TABLE 3

Three-day mortality of *Lygus hesperus* provided 45 μg *B.t.* PS201T6/mL

| Treatment | Initial number of live insects | Number of insects dead after 3 days | Percent of insects dead after 3 days |
|---|---|---|---|
| 15% sucrose solution | 25 | 7 | 28 |
| 45 μg *B.t.* PS201T6/mL of 15% sucrose solution | 25 | 17 | 68 |
| Starved (no food, water) | 25 | 25 | 100 |

TABLE 4

Two-day mortality of *Lygus hesperus* provided 4.5 μg *B.t.* PS201T6/mL

| Treatment | Initial number of live insects | Number of insects dead after 2 days | Percent of insects dead after 2 days |
|---|---|---|---|
| 15% sucrose solution | 50 | 29 | 58 |
| 4.5 μg *B.t.* PS201T6/mL of 15% sucrose solution | 50 | 41 | 82 |
| Starved (no food, water) | 50 | 50 | 100 |

Example 5—Activated Toxins from B.t.i.

The removal of a portion of the N-terminus of the 123D1 28 kDa toxin results in an advantageous activation of this toxin which increases the potency of its activity. Removal of amino acids can be accomplished by treatment with trypsin or other appropriate enzyme, or enzyme mixture, such as pronase or endogenous proteins in B.t. culture broths. Other biologically active fragments could be obtained by those skilled in the art using the teachings provided herein.

As those skilled in the art having the benefit of this disclosure would readily recognize, the specific media used to grow the B.t. culture can be modified to achieve optimum activation of the B.t. toxin. For example, the cell density can be modulated by adjusting or changing the culture medium. Also, media having proteases therein can be used to enhance the activation of the B.t. toxins.

Example 6—Insertion of Toxin Genes Into Plants

One aspect of the subject invention is the transformation of plants with genes encoding a toxin active against hemipteran pests. The transformed plants are resistant to attack by hemipterans.

Genes encoding hemipteran-active toxins, as disclosed herein, can be modified for optimum expression in plant, linked to a plant selectable marker gene, and inserted into a genome of plant cell using a variety of techniques which are well known to those skilled in the art. Any plant may be used in accordance with this invention, including angiosperms, gymnosperms, monocotyledons and dicotyledons. Preferred plants include cotton, potato, alfalfa, maize, rice and wheat. The transformation method itself is not critical to the invention but may include transformation with T-DNA using *Agrobactrium tumefaciens* or *A. rhizogenes* as the transformation agent, liposome fusion, microinjection, microprojectile bombardment, chemical agent (PEG or calcium chloride)-assisted DNA uptake, or electroporation, as well as other possible methods. Reference may be made to the literature for full details of the known methods, especially Holsters et al., 1978; Fromm et al., 1985; Horsch et at., 1985; Herrera-Estrella et al., 1983; Crossway et al., 1986; Lin, 1966; and Steinkiss and Stabel, 1983.

Use of a plant selectable marker in transformation allows for selection of transformed cells rather than cells that do not contain the inserted DNA. Various markers exist for use in plant cells and generally provide resistance to a biocide or antibiotic, including but not limited to, kanamycin, G418, hygromycin, and phosphinothricin. Visual markers including but not limited to b-glucuronidase, b-galactosidase, B-peru protein and luciferase may also be used. After transformation, those cells that have the DNA insert can be selected for by growth in a defined medium and assayed for marker expression, whether by resistance or visualization. Cells containing the DNA insert can be regenerated into plants. As long as stably transformed plants are obtained, the method used for regeneration will depend on the plant tissue and transformation method used and is not critical to the invention. However, for example, where cell suspensions have been used for transformation, transformed cells can be induced to produce calli and the calli subsequently induced to form shoots, which may then be transferred to an appropriate nutrient medium to regenerate plants. Alternatively, explants such as hypocotyl tissue or embryos may be transformed and regenerated by shoot induction in the appropriate media, followed by root and whole plant formation. Whatever regeneration method is used, the result will be stably transformed plants that can vegetatively and sexually transmit the transformed trait(s) to progeny, so that, if necessary, the transformed plant can be crossed with untransformed plants in order to transfer the trait to more appropriate germplasm for breeding purposes.

Example 7—Cloning of Novel B.t. Genes Into Insect Viruses

A number of viruses are known to infect insects. These viruses include, for example, baculoviruses and entomopoxviruses. In one embodiment of the subject invention, hemipteran-active genes, as described herein, can be placed within the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 795 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: neoleoensis
        ( C ) INDIVIDUAL ISOLATE: PS201T6

( v i i ) IMMEDIATE SOURCE:
        ( A ) LIBRARY: LambdaGem (TM)-11 library of Kenneth E. Narva
        ( B ) CLONE: 201T635

( x i ) SEQUENCE DESCRIPTION: SEQ ID NO:1:

```
ATGAAAGAGT  CAATTTACTA  CAATGAAGAA  AATGAAATAC  AAATTTCACA  AGGAAACTGT    60

TTCCCAGAAG  AATTAGGACA  TAATCCTTGG  AGACAACCTC  AATCCACAGC  AAGAGTTATT   120

TATTTAAAAG  TAAAAGATCC  TATTGATACT  ACTCAATTAT  TAGAAATAAC  AGAAATCGAA   180

AATCCCAATT  ATGTATTACA  AGCTATTCAA  CTAGCTGCTG  CCTTCCAAGA  TGCATTAGTA   240

CCAACTGAAA  CAGAATTTGG  AGAAGCCATT  AGATTAGTA   TGCCTAAAGG  ATTAGAAGTT   300

GCAAAAACTA  TTCAACCTAA  GGGTGCTGTT  GTTGCTTACA  CAGATCAAAC  TCTGTCACAA   360

AGCAACAACC  AAGTTAGTGT  TATGATTGAT  AGAGTTATTA  GTGTTTAAA   AACTGTAATG   420

GGAGTAGCTC  TTAGTGGTTC  CATTATAACT  CAATTAACAG  CTGCTATCAC  TGATACTTTT   480

ACAAACCTTA  ATACACAAAA  AGATTCTGCT  TGGGTTTTTT  GGGGAAAAGA  AACTTCACAT   540

CAAACAAATT  ACACATATAA  TGTCATGTTT  GCAATTCAAA  ATGAAACAAC  TGGACGCGTA   600

ATGATGTGTG  TACCTATTGG  ATTTGAAATT  AGAGTATTTA  CTGATAAAAG  AACAGTTTTA   660

TTTTTAACAA  CTAAAGATTA  CGCTAATTAT  AGTGTGAATA  TTCAAACCCT  AAGGTTTGCT   720

CAACCACTTA  TTGATAGCAG  AGCACTTTCA  ATTAATGATT  TATCAGAAGC  ACTTAGATCT   780

TCTAAATATT  TATAC                                                       795
```

( 2 ) INFORMATION FOR SEQ ID NO:2:

( i ) SEQUENCE CHARACTERISTICS:
        ( A ) LENGTH: 265 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
  ( A ) ORGANISM: Bacillus thuringiensis
  ( B ) STRAIN: neoleoensis
  ( C ) INDIVIDUAL ISOLATE: PS201T6

( v i i ) IMMEDIATE SOURCE:
  ( A ) LIBRARY: LambdaGem (TM)-11 Library of Kenneth E. Narva
  ( B ) CLONE: 201T635

( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Glu | Ser | Ile | Tyr | Tyr | Asn | Glu | Glu | Asn | Glu | Ile | Gln | Ile | Ser |
| 1 | | | | 5 | | | | | 10 | | | | | 15 | |
| Gln | Gly | Asn | Cys | Phe | Pro | Glu | Glu | Leu | Gly | His | Asn | Pro | Trp | Arg | Gln |
| | | | 20 | | | | 25 | | | | | 30 | | | |
| Pro | Gln | Ser | Thr | Ala | Arg | Val | Ile | Tyr | Leu | Lys | Val | Lys | Asp | Pro | Ile |
| | | | 35 | | | | 40 | | | | | 45 | | | |
| Asp | Thr | Thr | Gln | Leu | Leu | Glu | Ile | Thr | Glu | Ile | Glu | Asn | Pro | Asn | Tyr |
| | | 50 | | | | | 55 | | | | | 60 | | | |
| Val | Leu | Gln | Ala | Ile | Gln | Leu | Ala | Ala | Ala | Phe | Gln | Asp | Ala | Leu | Val |
| 65 | | | | | 70 | | | | | 75 | | | | | 80 |
| Pro | Thr | Glu | Thr | Glu | Phe | Gly | Glu | Ala | Ile | Arg | Phe | Ser | Met | Pro | Lys |
| | | | | 85 | | | | | 90 | | | | | 95 | |
| Gly | Leu | Glu | Val | Ala | Lys | Thr | Ile | Gln | Pro | Lys | Gly | Ala | Val | Val | Ala |
| | | | | 100 | | | | | 105 | | | | | 110 | |
| Tyr | Thr | Asp | Gln | Thr | Leu | Ser | Gln | Ser | Asn | Asn | Gln | Val | Ser | Val | Met |
| | | | 115 | | | | | 120 | | | | | 125 | | |
| Ile | Asp | Arg | Val | Ile | Ser | Val | Leu | Lys | Thr | Val | Met | Gly | Val | Ala | Leu |
| | | 130 | | | | | 135 | | | | | 140 | | | |
| Ser | Gly | Ser | Ile | Ile | Thr | Gln | Leu | Thr | Ala | Ala | Ile | Thr | Asp | Thr | Phe |
| 145 | | | | | 150 | | | | | 155 | | | | | 160 |
| Thr | Asn | Leu | Asn | Thr | Gln | Lys | Asp | Ser | Ala | Trp | Val | Phe | Trp | Gly | Lys |
| | | | | 165 | | | | | 170 | | | | | 175 | |
| Glu | Thr | Ser | His | Gln | Thr | Asn | Tyr | Thr | Tyr | Asn | Val | Met | Phe | Ala | Ile |
| | | | 180 | | | | | 185 | | | | | 190 | | |
| Gln | Asn | Glu | Thr | Thr | Gly | Arg | Val | Met | Met | Cys | Val | Pro | Ile | Gly | Phe |
| | | | 195 | | | | 200 | | | | | 205 | | | |
| Glu | Ile | Arg | Val | Phe | Thr | Asp | Lys | Arg | Thr | Val | Leu | Phe | Leu | Thr | Thr |
| | | | 210 | | | | 215 | | | | | 220 | | | |
| Lys | Asp | Tyr | Ala | Asn | Tyr | Ser | Val | Asn | Ile | Gln | Thr | Leu | Arg | Phe | Ala |
| 225 | | | | | 230 | | | | | 235 | | | | | 240 |
| Gln | Pro | Leu | Ile | Asp | Ser | Arg | Ala | Leu | Ser | Ile | Asn | Asp | Leu | Ser | Glu |
| | | | | 245 | | | | | 250 | | | | | 255 | |
| Ala | Leu | Arg | Ser | Ser | Lys | Tyr | Leu | Tyr | | | | | | | |
| | | | 260 | | | | | 265 | | | | | | | |

( 2 ) INFORMATION FOR SEQ ID NO:3:

( i ) SEQUENCE CHARACTERISTICS:
    ( A ) LENGTH: 222 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
  ( A ) ORGANISM: Bacillus thuringiensis
  ( B ) STRAIN: neoleoensis
  ( C ) INDIVIDUAL ISOLATE: PS201T6

( x i ) SEQUENCE DESCRIPTION: SEQ ID NO:3:

| | | | | | | | | | | | | | | |
|---|---|---|---|---|---|---|---|---|---|---|---|---|---|---|
| Val 1 | Lys | Asp | Pro | Ile 5 | Asp | Thr | Thr | Gln | Leu 10 | Leu | Glu | Ile | Thr | Glu 15 | Ile |
| Glu | Asn | Pro | Asn 20 | Tyr | Val | Leu | Gln | Ala 25 | Ile | Gln | Leu | Ala | Ala 30 | Ala | Phe |
| Gln | Asp | Ala 35 | Leu | Val | Pro | Thr | Glu 40 | Thr | Glu | Phe | Gly | Glu 45 | Ala | Ile | Arg |
| Phe | Ser 50 | Met | Pro | Lys | Gly | Leu 55 | Glu | Val | Ala | Lys | Thr 60 | Ile | Gln | Pro | Lys |
| Gly 65 | Ala | Val | Val | Ala | Tyr 70 | Thr | Asp | Gln | Thr | Leu 75 | Ser | Gln | Ser | Asn | Asn 80 |
| Gln | Val | Ser | Val | Met 85 | Ile | Asp | Arg | Val | Ile 90 | Ser | Val | Leu | Lys | Thr 95 | Val |
| Met | Gly | Val | Ala 100 | Leu | Ser | Gly | Ser | Ile 105 | Ile | Thr | Gln | Leu | Thr 110 | Ala | Ala |
| Ile | Thr | Asp 115 | Thr | Phe | Thr | Asn | Leu 120 | Asn | Thr | Gln | Lys | Asp 125 | Ser | Ala | Trp |
| Val | Phe 130 | Trp | Gly | Lys | Glu | Thr 135 | Ser | His | Gln | Thr | Asn 140 | Tyr | Thr | Tyr | Asn |
| Val 145 | Met | Phe | Ala | Ile | Gln 150 | Asn | Glu | Thr | Thr | Gly 155 | Arg | Val | Met | Met | Cys 160 |
| Val | Pro | Ile | Gly | Phe 165 | Glu | Ile | Arg | Val | Phe 170 | Thr | Asp | Lys | Arg | Thr 175 | Val |
| Leu | Phe | Leu | Thr 180 | Thr | Lys | Asp | Tyr | Ala 185 | Asn | Tyr | Ser | Val | Asn 190 | Ile | Gln |
| Thr | Leu | Arg 195 | Phe | Ala | Gln | Pro | Leu 200 | Ile | Asp | Ser | Arg | Ala 205 | Leu | Ser | Ile |
| Asn | Asp 210 | Leu | Ser | Glu | Ala | Leu 215 | Arg | Ser | Ser | Lys | Tyr 220 | Leu | Tyr | | |

REFERENCES

U.S. Patents

U.S. Pat. No. 4,448,885.
U.S. Pat. No. 4,467,036.
U.S. Pat. No. 4,695,455.
U.S. Pat. No. 4,695,462.
U.S. Pat. No. 4,797,276.
U.S. Pat. No. 4,849,217.
U.S. Pat. No. 4,853,331.
U.S. Pat. No. 4,918,006.
U.S. Pat. No. 4,948,734.
U.S. Pat. No. 5,135,867.
U.S. Pat. No. 5,151,363.
U.S. Pat. No. 5,273,746.
U.S. Pat. No. 5,298,245.
U.S. Pat. No. 5,302,387.

Foreign Patent Documents

EP 0 409 438.
EP 0 626 809.

Other References

Arnett, R. H., Jr. (1985) *American Insects*, Van Nostrand Reinhold Co., Inc., N.Y.

Beegle, C. C., (1978) "Use of Entomogenous Bacteria in Agroecosystems," *Developments in Industrial Microbiology* 20:97–104.

Couch, T. L. (1980) "Mosquito Pathogenicity of *Bacillus thuringiensis* var. *israelensis*," *Developments in Industrial Microbiology* 22:61–76.

Crossway et al. (1986) *Biotechniques* 4:320–334.

Feitelson, J. S., J. Payne, L. Kim (1992) *Bio/Technology* 10:271–275.

Fromm et al. (1985) *PNAS* 82:5824–5828.

Gaertner, F. H. (1989) "Cellular Delivery Systems for Insecticidal Protiens: Living and Non-Living Microorganisms," in *Controlled Delivery of Crop Protection Agents*, R. M. Wilkins, ed., Taylor and Francis, New York and London, 1990, pp. 245–255.

Gaertner, F. H., L. Kim (1988) *TIBTECH* 6:S4-S7.

Herrera-Estrella et al. (1983) *Nature* 303:209–313.

Höfte, H., H. R. Whiteley (1989) *Microbiological Reviews* 52(2):242–255.

Lambert, B., H. Höfte, K. Annys, S. Jansens, P. Soetaert, M. Peferoen (1992) "Novel *Bacillus thuringiensis* insecticidal crystal protein with a silent activity against coleopteran larvae," *Appl. Environ. Microbiol.* 58:2536–2542.

Holsters et al. (1978) *Mol. Gen. Genet.* 163:181–187.

Horsch et al. (1978) *Science* 228:1229–1231.

Jacquet, J., R. Hutter, P. Luthy (1987) "Specificity of *Bacillus thuringiensis* delta-endotoxin," *Appl. Environ. Microbial.* 53:500–504.

Krieg, A., A. M. Huger, G. A. Langenbruch, W. Schnetter (1983) *Z. ang. Ent.* 96:500–508.

Lin (1966) *Science* 151:333–337.

Martens, J. W. M., G. Honee, D. Zuidema, J. W. M. van Lent, B. Visser, J. M. Vlak (1990) *Appl. Environmental Microbial.* 56(9):2764–2770.

Merryweather, A. T., U. Weyer, M. P. G. Harris, M. Hirst, T. Booth, R. D. Possee (1990) *J. Gen. Virol.* 71:1535–1544.

Prefontaine, G., P. Fast, P. C. K. Lau, M. A. Hefford, Z. Hanna, R. Brosseau (1987) *Appl. Environ. Microbiol.* 53(12):2808–2814.

Schnepf, H. E., H. R. Whiteley (1981) *Proc. Natl. Acad. Sci. USA* 78:2893–2897.

Steinkiss and Stable (1983) *Protoplasma* 116:222–227.

We claim:

1. A method of killing hemipteran insect pests which comprises administering to said pests, or the environment of said pests, a pesticidally effective amount of a *Bacillus thuringiensis* toxin, wherein said toxin is from PS201T6.

2. A method of killing hemipteran insect pests which comprises administering to said pests, or the environment of said pests, a pesticidally effective amount of a *Bacillus thuringiensis* toxin, wherein said *Bacillus thuringiensis* toxin is an activated toxin, and wherein said activation is effected by the truncation of a *Bacillus thuringiensis* strain PS201T6 toxin.

3. A method of killing hemipteran insect pests which comprises administering to said pests, or the environment of said pests, a pesticidally effective amount of a *Bacillus thuringiensis* toxin, wherein the *Bacillus thuringiensis* (B.t.) toxin is administered to the hemipteran insect pests in planta by inserting a B.t. insecticidal structural gene into the plant genome such that the B.t. toxin is expressed in the plant tissue which the hemipteran insect pest ingests, wherein said *Bacillus thuringiensis* gene encodes a PS201T6 toxin or a hemipteran-killing fragment thereof.

* * * * *

UNITED STATES PATENT AND TRADEMARK OFFICE
CERTIFICATE OF CORRECTION

PATENT NO. : 5,723,440
DATED : March 3, 1998
INVENTOR(S) : Brian Stockhoff and Christopher Conlan It is certified that error appears in the above-identified patent and that said Letters Patent is hereby corrected as shown below:

Column 2, line 34: "(L))." should read --(L.)).--.

Column 3, line 17: "contractile" should read --contractible--; and line 19: "hydrolyric" should read --hydrolytic--.

Col 5 line 43: "progeny, are fled." should read --progeny, are filed.--; and

Col 5 line 45: "fights" should read --rights--.

Column 8, line 20: "200 rpm. for" should read --200 rpm for--.

Column 9, line 27: "$\mu$g/mL. after two" should read --$\mu$g/mL after two--.

Column 17, line 4: "H. Höfte," should read --H.R. Höfte,.

Signed and Sealed this

Twentieth Day of October, 1998

Attest:

BRUCE LEHMAN

Attesting Officer     Commissioner of Patents and Trademarks